United States Patent [19]

Frank

[11] Patent Number: 4,877,912
[45] Date of Patent: * Oct. 31, 1989

[54] PROCESS FOR PREPARING 1,1,3,4,4,6-HEXAMETHYL-1,2,3,4-TETRAHYDRONAPHTHALENE

[75] Inventor: Walter C. Frank, Holland, Pa.

[73] Assignee: Union Camp Corporation, Wayne, N.J.

[*] Notice: The portion of the term of this patent subsequent to Oct. 31, 2006 has been disclaimed.

[21] Appl. No.: 303,356

[22] Filed: Jan. 27, 1989

[51] Int. Cl.⁴ .................... C07C 12/00; C07C 12/64; C07C 2/64
[52] U.S. Cl. .................................. 585/411; 585/410; 585/452; 585/459
[58] Field of Search ................ 585/410, 411, 452, 459

[56] References Cited

U.S. PATENT DOCUMENTS

| 3,246,044 | 4/1963 | Wood et al. | 260/668 |
| 3,379,785 | 4/1968 | Kahn | 260/668 |
| 3,865,875 | 12/1963 | Wood et al. | 585/410 |
| 3,992,432 | 11/1976 | Napier et al. | 260/465.1 |
| 4,284,818 | 8/1981 | Sato et al. | 568/323 |
| 4,551,573 | 11/1985 | Cobb | 585/459 |
| 4,767,882 | 8/1988 | Suzukamo et al. | 560/100 |

FOREIGN PATENT DOCUMENTS 2601670 2/1988 France .
57-40420 3/1982 Japan .
388527 3/1975 U.S.S.R. .

OTHER PUBLICATIONS

Boone et al., "The Acid-Catalyzed Alkylation and Cyclialkylation of the Cymenes with Isobutylene and Related Olefins", *J. Org. Chem.*, vol. 36, No. 15, pp. 2042-2048 (1971).
Coscia et al., "The Synthesis of 2,2-Ditolylpropane from α,p-dimethylstyrene", *J. Org. Chem.*, vol. 26, pp. 1398-1401 (1961).
Kondo et al., "Sulfonium Salts as Liquid-Liquid Phase-Transfer Catalysts", *Synthesis*, pp. 403-404 (1988).
Kennedy, *Carbocationic Polymerization*, p. 221 (Wiley-Interscience Publishers, 1982).

Primary Examiner—William R. Dixon, Jr.
Assistant Examiner—J. Saba
Attorney, Agent, or Firm—Edward J. Sites

[57] ABSTRACT

A process is disclosed for the production of 1,1,3,4,4,6-Hexamethyl-1,2,3,4-Tetrahydronaphthalene comprising reacting para-cymene with an olefinic compound selected from the group consisting of 2,3-dimethyl-1-butene and neohexene, in the presence of a reagent of the formula

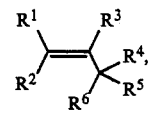

and further in the presence of an aluminum halide and $I_2$, wherein in the above formula, $R^1$, $R^2$, $R^3$, $R^4$, $R^5$ and $R^6$, independently, are H or a $C_1$-$C_3$ straight chain, or branched alkyl, provided that no more than one of $R^1$, $R^2$ and $R^3$ are H, and no more than one of $R^4$, $R^5$ and $R^6$ are H.

The subject process produces the desired compound in a surprisingly high yield, with a surprisingly high selectivity, and at a relatively high rate of reaction, using better, more convenient and/or less expensive process methodology than many processes known heretofore. Using the subject process, one is able to efficiently and effectively produce HMT, a compound of extreme importance to the fragrance industry.

10 Claims, No Drawings

PROCESS FOR PREPARING 1,1,3,4,4,6-HEXAMETHYL-1,2,3,4-TETRAHYDRONAPHTHALENE

BACKGROUND OF THE INVENTION

The present invention relates to an improved process for the production of 1,3,4,4,6-hexamethyl-1,2,3,4-tetrahydronaphthalene, referred to herein as HMT, for brevity.

HMT and other alkyl-substituted tetrahydronaphthalenes are of significant importance to the perfumery as well as other industries. By conventional acylation processes, HMT, for example, can be converted to 7-acetyl-1,1,3,4,4,6-hexamethyl-1,2,3,4-tetrahydronaphthalene, a well known musk perfume. Because of their clean musk fragrance and ability to retain that fragrance over long periods of time, these HMT derivatives are of great commercial value as synthetic musk perfume substitutes for the expensive, natural musk perfumes of the macrocyclic ketone series. Consequently, various synthetic methods have been proposed for the production of HMT and other related intermediates useful in the perfumery or other industries.

Cobb, U.S. Pat. No. 4,551,573 entitled "Alkylation of Aromatic Compounds" (the '573 patent), for example, broadly discloses a process for the alkylation and cylialkylation of aromatic compounds with olefinic compounds in the presence of a catalyst consisting essentially of aluminum halide and elemental iodine. Aromatic compounds described in the '573 patent include monocyclic, bicyclic or tricyclic aromatic compounds having 6 up to 30 carbon atoms, including compounds of the formula

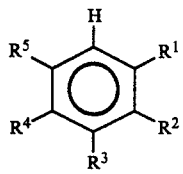

[V]

wherein each of $R^1$ through $R^5$ is independently selected from hydrogen and $C_1$ through $C_{10}$ alkyl or cycloalkyl radical. Particular aromatic compounds disclosed as useful are para-cymene, para-methylcyclohexylbenzene, para-methylcyclopentylbenzene, para-ethylcyclopentylbenzene, para-ethylcyclohexylbenzene, benzene, toluene, ortho- or meta-xylene and tertiary-butylbenzene. Suitable olefinic compounds discussed encompass organic compounds having at least one carbon-carbon double bond and any substituents which do not detrimentally interact with the catalyst employed the alkylation reaction. Preferred olefinic compounds include compounds of the Formula

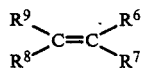

wherein each of $R^6$, $R^7$, $R^8$, and $R^9$ are independently selected from hydrogen and $C_1$ through $C_1$ alkyl or cycloalkyl radicals. In addition, $R^6$ and $R^7$ can be joined as part of a polymethylene radical or a halogen-, alkyl- or cycloalkyl-substituted polymethylene radical having about 2 to about 20 carbon atoms, i.e., a carbocyclic compound with an exocyclic double bond. Further, $R^6$ and $R^9$ can be similarly joined as part of a polymethylene radical or a halogen-, alkyl- or cycloalkyl-substituted polymethylene radical having about 2 to about 20 carbon atoms, i.e., a carbocyclic compound with an endocyclic double bond. Particularly specified are isobutylene, 2-methyl-1-butene, 2-methyl-2-butene, 2,3-dimethyl-2-butene, neohexene (3,3-dimethyl-1-butene), diiso- butylene-1, 2-butene, 2-pentene, 1-methylcyclohexene, 1-methylcyclopentene and 2-hexene. In addition, diisobutylene-2 is claimed as an olefinic compound, although it is not specified in the text of the patent. The patent also notes that a mixture of olefinic compounds can be employed, in which case one of the olefins may function as a sacrificial agent. A combination of neohexene and isobutylene is a suggested mixture of such olefins. Suitable aluminum halide compounds include aluminum tribromide, dichloroaluminum bromide, dibromoaluminum fluoride, aluminum triiodide, and aluminum chloride, with aluminum chloride being preferred. The products of the reactions described in the '573 patent encompass aromatic compounds represented by the Formula

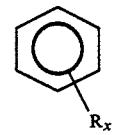

wherein each R is independently a $C_1$ through $C_{40}$ alkyl or cycloalkyl radical and x is an integer from at least one up to 6. One or more of the R groups may be halogen, but not all R groups of the product are halogen. Particular compounds specified include tertiary-butyl-meta-xylene, di-tertiary-butyl-toluene, tertiary-amyl-xylene, secondary-hexyl-xylene, and tertiary-hexyl-xylene. Other products include indanes of the general structure

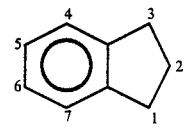

and tetrahydronaphthalene compounds of the general Formula

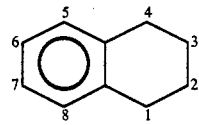

such indanes and tetrahydronaphthalenes having widely varying substitution patterns. Specific indanes and tetrahydronaphthalenes include 1,1,3,4,4,6-hexamethyl-1,2,3,4-tetrahydronaphthalene, 1,1,3,3,5-pentamethylindane, 1,1,2,3,3,5-hexamethylindane and 1,1,3,5,5-pentamethylindane.

Other synthetic methods include those described in Wood et al., U.S. Pat. No. 3,856,875 entitled "Process for Producing 1,1,3,4,4,6-Hexamethyl-1,2,3,4Tetrahydronapthalene [sic](HMT)", which discloses a process for the preparation of HMT wherein an equivalent or excess amount of para-cymene is reacted with a substantially equal molar solution of neohexene and a tertiary alkyl halide in the presence of an effective amount of an anhydrous aluminum halide catalyst suspended in a reaction-compatible solvent. Although any tertiary alkyl halide can be employed in the disclosed process, tertiary butyl chloride, tertiary amyl chloride and 2,5-dichloro-2,5-dimethylhexane are noted as preferred. The process is described as having a solvent dependency, with the satisfactory solvents being ethylene dichloride, chloroform, methylene dichloride, 1,1,2,2-tetrachloroethane, 1,2-dichloroethylene, 1,2,3-trichloropropane, 1,1,2-trichloroethane, monochlorobenzene, fluorobenzene, ortho-dichlorobenzene, and para-xylene. Numerous solvents were deemed unsatisfactory for use in the disclosed process, such solvents including nitromethane, benzene, nitrobenzene, para-cymene, n-hexane, 1,2,2-trichloroethylene, carbon tetrachloride, 1,1,1-trichloroethane, carbon disulfide, 1,1,2,2,2-pentachloroethane, 1,2-dichloropropane, 1,1-dichloroethylene, and 1,1-dichloroethane. These unsatisfactory solvents are said to yield substantially poorer results.

Wood, U.S. Pat. No. 3,246,044 entitled "Process for Making 1,1,3,4,4,6-Hexamethyl-1,2,3,4Tetrahydronaphthalene," discloses a process for preparing HMT which includes reacting an alpha para-dimethylstyrene derivative such as dimethyl-para-tolyl-carbinyl halide, and neohexene in the presence of a catalyst such as aluminum chloride, aluminum bromide and ferric chloride, or other Friedel-Crafts catalysts, at low temperatures. Suitable solvents are listed as ethylene dichloride or carbon tetrachloride, or other inert chlorinated hydrocarbon solvents. It is noted that other solvents such as nitrobenzene and nitromethane, may be used, but the yield of desired product is indicated as generally being lower when such solvents are employed.

Sato et al., U.S. Pat. No. 4,284,818 entitled "Process for Preparing Hexamethyltetrahydronaphthalenes," describes a process for producing HMT comprising reacting para-cymene with a 2,3-dimethyl butene using a catalytic amount of anhydrous aluminum halide in the presence of a secondary alkyl halide, tertiary alkyl halide, propargyl halide or allyl halide. It is noted that both the 2,3-dimethyl-1-butene and 2,3-dimethyl-2-butene can be employed as the 2,3-dimethyl butene reagent, however, 2,3-dimethyl-1-butene was said to yield better results. The reaction is generally carried out using a solvent, such solvents including aliphatic hydrocarbons, halogenated aromatic hydrocarbons, and halogenated aliphatic hydrocarbons.

Japanese Pat. Publication SHO 57-40420 discusses a method of making HMT characterized by reacting para-cymene and neohexene in the presence of anhydrous aluminum halide as catalyst. Suitable anhydrous aluminum halides are said to include aluminum chloride. The reaction is generally carried in a solvent, however, it is noted that it is possible to conduct the reaction without any additional solvent using excess para-cymene. Examples of suitable solvents are methylene chloride, ethylene chloride, chloroform and other inactive fatty hydrocarbon halides. Other solvents such as aromatic hydrocarbon halides, fatty hydrocarbons, aromatic hydrocarbons, etc., can be used, but it is noted that the use of such solvents generally lowers the yield of the desired end product.

Kahn, U.S. Pat. No. 3,379,785 entitled "Process for Preparing Polyalkyltetrahydronaphthalenes," relates to a process for preparing polyalkyl tetrahydronaphthalenes, and more specifically, a process for preparing HMT. The process involves the reaction of a substituted styrene and a 2,3-dimethylbutene, said reaction being carried out at elevated temperatures and in the presence of a cation exchange resin. The 2,3-dimethylbutene reactant employed is disclosed as comprising either 2,3-dimethyl-1-butene, 2,3-dimethyl-2-butene, or mixtures thereof. The preferably employed solvent comprises an aromatic hydrocarbon, such as, for example, benzene, toluene, ethylbenzene, or a xylene.

Suzukamo et al., U.S. Pat. No. 4,767,882 entitled "Tetrahydronaphthalene Derivatives and Their Production," discloses a process for preparing a tetrahydronaphthalene derivative in an optically active state which comprises reacting a benzene compound and a pyrocine compound in the presence of a Lewis acid, or, alternatively, reacting the benzene with the pyrocine compound in the presence of an acid catalyst followed by treatment of the resultant product with the Lewis acid.

The particular processes detailed in these patents suffer from various drawbacks, including low conversion of reactants, poor selectivity to the desired products, or sluggish reaction rates. New and/or better processes, especially processes for the production of HMT, are needed. The present invention is directed to this important end.

SUMMARY OF THE INVENTION

The present invention involves a cyclialkylation process for the production of HMT comprising contacting para-cymene with an olefinic compound selected from the group consisting of 2,3-dimethyl-1-butene and neohexene, in the presence of a reagent of the formula

and further in the presence of an aluminum halide and $I_2$, wherein in the above formula, $R^1$, $R^2$, $R^3$, $R^4$, $R^5$ and $R^6$, independently, are H or a $C_1$–$C_3$ straight chain, or branched alkyl, provided that no more than one of $R^1$, $R^2$ and $R^3$ are H, and no more than one of $R^4$, $R^5$ and $R^6$ are H.

The subject process produces HMT in a surprisingly high yield, with a surprisingly high selectivity, and at a relatively high rate of reaction, using better, more convenient and/or less expensive process methodology than many processes known heretofore. Using the subject process, one is able to efficiently and effectively produce HMT, a compound of extreme importance to the fragrance industry.

DETAILED DESCRIPTION OF THE INVENTION

As noted above, the present invention is directed to a novel and particularly useful cyclialkylation process for the production of 1,1,3,4,4,6-hexamethyl, 1,2,3,4-tetrahydronaphthalene, referred to herein as HMT, a compound of the formula

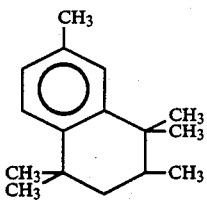

[I]

In accordance with the present invention, HMT is produced by reacting para-cymene, a compound of the formula

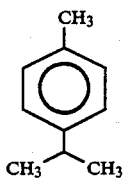

[II]

with an olefinic compound selected from the group consisting of 2,3-dimethyl-1-butene, a compound of the formula

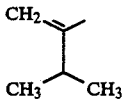

[III]

and neohexene (3,3-dimethyl-1-butene), a compound of the formula

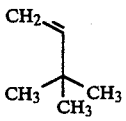

[IV]

or mixtures of the 2,3-dimethyl-1-butene and neohexene compounds.

It has been found that when a small and select group of reagents are employed in the process, such as those components of the formula

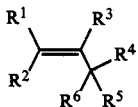

[V]

wherein $R^1$, $R^2$, $R^3$, $R^4$, $R^5$ and $R^6$, independently, are H or a $C_1$–$C_3$ straight chain, or branched alkyl, provided that no more than one of $R^1$, $R^2$ and $R^3$ are H, and no more than one of $R^4$, $R^5$ and $R^6$ are H, surprisingly high yields of and selectivity of HMT can be achieved, with the process proceeding at a relatively high reaction rate. In a most preferred embodiment, the Formula V compound is 2,4,4-trimethyl-2-pentene (that is, diisobutylene-2, a compound of Formula V wherein $R^1$, $R^2$, $R^4$, $R^5$ and $R^6$ are methyl and $R^3$ is H). The Formula V compounds have been found to be surprisingly effective in promoting the efficiency of the subject process, resulting in higher yields and selectivity than heretofore expected.

Although the precise details of the reaction mechanism are unclear, it is believed that the Formula V compounds are capable of preferentially carrying out a necessary hydride abstraction function, leaving the 2,3-dimethyl-1-butene and neohexen compounds to preferentially participate in the cyclialkylation step of the subject process. Such discriminating activity is thought to result from the particular steric conformation and electron releasing properties of the specific class of Formula V. compounds outlined herein, as compared with the 2,3-dimethyl-1-butene and neohexene compounds employed in the subject process as alkylating agents. The resultant process therefore has a smaller amount of side reactions occurring, and a higher selectivity to and yield of the desired HMT end product.

It should also be noted that the subject process is employing in a non-productive reduction (hydride abstraction) step a more readily available, less expensive reagent, in lieu, at least in part, of the less readily available, more expensive alkyl halide compounds consumed in accordance with some prior art procedures. As a result, one is able to avoid excessive formation of hydrogen halides and accumulation of such compounds in the product stream, an undesirable result associated with some art processes. Moreover, the potential for corrosion problems within the reaction system concomitant with the formation of he hydrogen halides may be lessened, and the need for complex procedures for the separation of the desired product from the hydrogen halide by-products may be minimized.

Any aluminum halide is suitable for use in the present process. Such aluminum halides include aluminum chloride, aluminum bromide, aluminum iodide, monofluorodichloroaluminum, monobromodichloroaluminum, monoiododichloroaluminum, monofluorodibromoaluminum, and the like. Of these aluminum halides, aluminum chloride and aluminum bromide, particularly aluminum chloride, are preferred.

As noted above, the process must also be conducted in the presence of elemental iodine ($I_2$)

In general, the molar proportions of the reagents employed in the present process can be varied over a relatively wide range. By way of guidance, however, it is preferable to use a mixture of the 2,3-dimethyl-1butene and/or neohexene olefinic compound, and the Formula V reagent, wherein these components are present in a molar range of about 1.0 to about 5.0 moles of olefin per mole of reagent V. More preferably, the 2,3- dimethyl-1-butene and/or neohexene, and the reagent V, are present in nearly equimolar amounts, that is, about 1.0 mole of 2,3-dimethyl-1-butene and/or neohexene per mole of reagent V.

Preferably, the para-cymene is present in a range of about 0.5 to about 10 moles per mole of 2,3-dimethyl1-butene and/or neohexene. More preferably, the paracymene is present in a range of about 0.5 to about 5.0 per mole of 2,3-dimethyl-1-butene and/or neohexene.

The amount of aluminum halide utilized is preferably in the range of about 2% to about 10% by weight based on the combined weight of the para-cymene, the 2,3-dimethyl-1-butene and/or neohexene, and the Formula V reagent.

The amount of $I_2$ employed is preferably in the range of about 1% to about 100% by weight based upon the weight of the aluminum halide employed. Most preferably, the $I_2$ is about 10% to about 50% of the weight of the aluminum halide employed.

The reaction may be carried out using a solvent, although, if desired, para-cymene, one of the starting materials, may be employed in large excess in lieu of an additional solvent. A number of different solvents may be utilized in the present invention, including halogenated and unhalogenated aliphatic, alicyclic and aromatic hydrocarbon solvents.

Where the process is run using neohexene, in whole or in part, as the alkylating agent, such halogenated aliphatic, halogenated alicyclic and halogenated aromatic hydrocarbon solvents are preferred, for reasons of increased yield. Representative of the halogenated solvents are the aliphatic solvents methylene chloride, chloroform, carbon tetrachloride, ethylene chloride, ethylidene chloride, 1,1,1-trichloroethane, 1,1,2-trichloroethane, 1,1,2,2-tetrachloroethane, 1,2-dichloroethylene, trichloroethylene, tetrachloroethylene, 1,2,3-trichloropropane, amyl chloride, and ethylene bromide, and the aromatic solvents monochlorobenzene, ortho-dichlorobenzene, bromobenzene and fluorobenzene.

Where 2,3-dimethyl-1-butene is employed as the alkylating agent in the subject process, the unhalogenated aliphatic, unhalogenated alicyclic and unhalogenated aromatic hydrocarbon solvents are preferred, for reasons of increased yield and/or safety. Exemplary of the unhalogenated solvents are the aliphatic solvents n-hexane, n-heptane and n-octane, the alicyclic solvent cyclohexane, and the aromatic solvents benzene, toluene, ethylbenzene and xylene. Particularly preferred for reasons of yield, safety and/or process engineering are the unhalogenated aliphatic and unhalogenated alicyclic hydrocarbons.

Other suitable halogenated and unhalogenated solvents are described, for example, in U.S. Pat. Nos. 4,284,818, 3,856,875 and 3,379,785, the disclosures of which are incorporated herein by reference.

The cyclialkylation reaction of the invention can be carried out in any suitable vessel which provides efficient contacting between the aluminum halide and the other reactants. For simplicity, a stirred batch reactor can be employed. Stirring is recommended to provide efficient contact between reactants. Moreover, the reaction vessel used should be resistant to the possibly corrosive nature of the aluminum halide. Glass-lined vessels would be suitable for this purpose. Additional vessel materials will be apparent to those skilled in the art.

Ideally, the reaction is carried out at temperatures ranging from about 20° C. to about 80° C., preferably at temperatures ranging from about 30° C. to about 65° C., and most preferably at a temperature of about 35° C.

The pressure at which the reaction is carried out is not critical. If the reaction is carried out in a sealed vessel, autogenous pressure is acceptable, although higher or lower pressures, if desired, may be employed. The reaction can also be carried out at atmospheric pressure in an open reaction vessel, in which case the vessel is preferably equipped with a moisture trap to prevent significant exposure of the aluminum halide to moisture. The reaction can take place in an oxygen atmosphere, or an inert atmosphere as in the presence of a gas such as nitrogen, argon and the like, such inert atmospheres being preferred.

Reaction time is generally rather short and is often dictated by the kind of equipment employed. Sufficient time must be provided, however, for thorough contacting of the para-cymene, the 2,3-dimethyl-1-butene and/or neohexene, the aluminum halide and the $I_2$. Generally the reaction proceeds to completion in about 1 to about 7 hours.

Product can be recovered by first quenching the reaction mixture in cold water or on crushed ice, preferably on ice, and then processing the mixture in the usual manner for Friedel-Crafts reactions to extract the HMT. Suitable extraction protocol is described, for example, in *Friedel-Crafts Reactions*. Typically, following quenching and the resultant phase separation, the organic layer is washed an additional time with water to aid in removal of the Lewis acid. One or more additional washings can be carried out with dilute alkali solution to further aid Lewis acid removal. The organic layer can also be washed, if desired, with dilute sodium thiosulfate solution to assist in the removal of any residual $I_2$. Pure product can then be recovered by subjecting the washed reaction mixture to reduced pressure fractional distillation.

The HMT prepared in accordance with the processes of the invention, as hereinbefore indicated, may, for example, be acylated to obtain acylated HMT, that is, 7-acetyl-1,1,3,4,4,6-hexamethyl-1,2,3,4tetrahydronaphthalene, a compound having a very fine, musk-like fragrance, a characteristic which renders it highly valuable for use in the perfumery industry. The acylation process may be carried out using conventional methods, such as by reacting the HMT with an acyl halide or acid anhydride in the presence of an acid-acting catalyst. Suitable acylation methods are well known in the art and are disclosed, for example, in U.S. Pat. No. 4,284,818.

The present invention is further described in the following Examples. These Examples are not to be construed as limiting the scope of the appended claims.

In each example, the reaction flasks were equipped with a condenser, mechanical stirrer, addition funnel and thermocouple/ temperature controller connected to an automatic laboratory jack. The flasks were cooled, when necessary, with a dry ice/isopropanol bath. The flask contents were continuously stirred throughout the reaction.

Results were analyzed on both polar and non-polar gas chromatography columns. All gas chromatography analyses were carried out on capillary columns using a weight percent internal standard method of analysis. Structure identifications were assigned based on GCMS fragmentation patterns compared to standards.

Example 3 is provided for comparative purposes only, and does not illustrate processes of the present invention. Example 3 was carried out substantially in accordance with the procedures set forth in U.S. Pat. No. 4,551,573. Examples 1 and 2 are examples of processes of the present invention.

EXAMPLES

Example 1

A 100 ml, four-necked, round bottom flask was charged with para-cymene (27.17 g). A mixture of 2,3 dimethyl-1-butene and diisobutylene-2 was charged into a syringe. To the flask was added anhydrous aluminum chloride (1.455 g) and iodine (0.426 g), and the flask mixture was stirred for about 10 minutes. The syringe mixture was then added to the flask over about a 9 minutes period, with a total of 10.15 g of 2,3-dimethyl1-butene, and 10.26 g of diisobutylene-2 being delivered to the flask. During the addition of the syringe mixture, a temperature increase to about 35° C was observed. The flask mixture was allowed to cool to room temperature for about 18 minutes. The flask mixture was then stirred for about 33 minutes and quenched with 15 ml of deionized water. The organic phase was washed with, in order, 5% HCl, 10% $Na_2CO_3$, and 50% (halfsaturated) brine solution. The aqueous layers were individually extracted with ethyl ether, and the ether layers combined with the organic phase. The organics were then dried over $K_2CO_3$, filtered and evaporated to yield a crude product (34.08 g) containing 41.64 weight % HMT (55.30 % molar yield of HMT based on the amount of 2,3-dimethyl-1butene charged).

Example 2

A 100 ml, four-necked, round bottom flask was charged with para-cymene (27.17 g). To the flask was added anhydrous aluminum chloride (1.454 g) and iodine (0.424 g). A mixture of neohexene (10.15 g) and diisobutylene-2 (10.26 g) was then added over a period of about 23 minutes. An increase in temperature to about 35° C was observed during the addition. The reaction was stirred for about 38 minutes, then quenched with 15 ml of deionized water and worked up as described in Example 1 to yield a crude product (32.67 g) containing 51.97 weight % HMT (66.16 % molar yield of HMT based on the amount neohexene charged).

EXAMPLE 3 (Comparative Example)

A 100 ml, four-necked, round bottom flask was charged with para-cymene (27.17 g). To the flask was added anhydrous aluminum chloride (1.455 g) and iodine (0.427 g). A mixture of neohexene (10.14 g) and isobutylene (5.1 g), chilled by a dry ice/isopropanol bath, was then added over a period of about 17 minutes while maintaining a flask temperature of about 35° C. The reaction mixture was stirred for about 43 minutes, quenched with 15 ml of deionized water, and worked up as in Example 1 to yield a crude product (30.80 g) containing 22.59 weight % HMT (27.13 % molar yield of HMT based on the amount neohexene charged).

Various modifications of the invention in addition to those shown and described herein will be apparent to those skilled in the art from the foregoing description. Such modifications are also intended to fall within the scope of the appended claims.

What is claimed is:

1. A process for producing 1,1,3,4,4,6-hexamethyl-1,2,3,4,-tetrahydronaphhthalene comprising contacting para-cymene with 2,3-dimethyl-1-butene in the presence of a reagent of the Formula

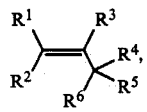

aluminum halide, and $I_2$, wherein $R^1$, $R^2$, $R^3$, $R^4$, $R^5$ and $R^6$, independently, are a a H or $C_1$-$C_3$ straight chain, or branched alkyl, provided that (i) no more than one of $R^1$, $R^2$, and $R^3$ are H, and (ii) no more than one of $R^4$, $R^5$ and $R^6$ are H.

2. A process of claim 1 wherein
$R^1$, $R^2$, $R^4$, $R^5$ and $R^6$ are each methyl, and
$R^3$ is H.

3. A process of claim 1 wherein said aluminum halide is selected from the group consisting of aluminum chloride, aluminum bromide, aluminum iodide, monofluorodichloroaluminum, monobromodichloroaluminum, monoiododichloroaluminum and monofluorodibromoaluminum.

4. A process of claim 3 wherein said aluminum halide is selected from the group consisting of aluminum chloride and aluminum bromide.

5. A process of claim 4 wherein, said aluminum halide is aluminum chloride.

6. A process for producing 1,1,3,4,4,6-Hexamethyl-1,2,3,4-Tetrahydronaphthalene comprising contacting para-cymene with neohexene in the presence of a reagent of the Formula

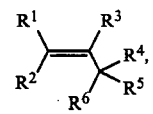

aluminum halide, and
$I_2$,
wherein
$R^1$, $R^2$, $R^3$, $R^4$, $R^5$ and $R^6$ independently are H or a $C_1$-$C_3$ straight chain, or branched alkyl, provided that (i) no more than one of $R^1$, $R^2$ and $R^3$ are H, and (ii) no more than one of $R^4$, $R^5$ and $R^6$ are H.

7. A process of claim 6 wherein
$R^1$, $R^2$, $R^4$, $R^5$ and $R^6$ are each methyl, and
$R^3$ is H.

8. A process of claim 6 wherein said aluminum halide is selected from the group consisting of aluminum chloride, aluminum bromide, aluminum iodide, monofluorodichloroaluminum and momobromodichloroaluminum, monoiododichloroaluminum and monofluorodibromoaluminum.

9. A process of claim 8 wherein said aluminum halide is selected from the group consisting of aluminum chloride and aluminum bromide.

10. A process of claim 9 wherein said aluminum halide is aluminum chloride.

* * * * *